United States Patent
Cutrer

(10) Patent No.: US 9,283,402 B2
(45) Date of Patent: Mar. 15, 2016

(54) APPARATUS AND METHOD FOR PROVIDING A DOUBLE BALLOON BREAST BRACHYTHERAPY DEVICE

(75) Inventor: Lloyd Michael Cutrer, Huntington Beach, CA (US)

(73) Assignee: Best Medical International, Inc., SpringField, VA (US)

(*) Notice: Subject to any disclaimer, the term of this patent is extended or adjusted under 35 U.S.C. 154(b) by 0 days.

(21) Appl. No.: 12/983,429

(22) Filed: Jan. 3, 2011

(65) Prior Publication Data
US 2012/0172651 A1  Jul. 5, 2012

(51) Int. Cl.
*A61N 5/00* (2006.01)
*A61N 5/10* (2006.01)

(52) U.S. Cl.
CPC .................... *A61N 5/1015* (2013.01)

(58) Field of Classification Search
CPC ............... A61N 5/1015; A61N 2005/1018; A61N 2005/1005; A61N 2005/1021; A61M 2210/0687; A61M 2230/005; A61M 2025/1013; A61M 2025/1075; A61M 25/1011
USPC ............ 600/1, 4, 3, 7, 2, 8, 564, 567, 6, 104, 600/15, 19, 41, 431, 562, 563, 566, 568, 9; 604/101.02, 103.02, 104, 164.01, 604/164.08, 309, 35, 43, 45, 523, 540, 57, 604/912, 913, 915, 96.01; 128/897–899
See application file for complete search history.

(56) References Cited

U.S. PATENT DOCUMENTS

| 5,653,683 | A | 8/1997 | D'Andrea |
| 5,720,717 | A | 2/1998 | D'Andrea |
| 5,913,813 | A * | 6/1999 | Williams et al. .................. 600/3 |
| 6,616,629 | B1 | 9/2003 | Verin et al. |
| 6,923,754 | B2 | 8/2005 | Lubock |
| 6,955,641 | B2 | 10/2005 | Lubock |
| 7,357,770 | B1 | 4/2008 | Cutrer et al. |
| 8,251,884 | B2 | 8/2012 | Lubock et al. |
| 8,277,370 | B2 | 10/2012 | Quick |
| 8,287,442 | B2 | 10/2012 | Quick |
| 8,348,825 | B2 | 1/2013 | Partridge et al. |
| 8,360,950 | B2 | 1/2013 | Acosta et al. |
| 8,568,284 | B2 | 10/2013 | White et al. |
| 2004/0087827 | A1 * | 5/2004 | Lubock ............................. 600/3 |
| 2008/0221384 | A1 * | 9/2008 | Chi Sing et al. .................. 600/7 |
| 2009/0143634 | A1 * | 6/2009 | Benson et al. .................... 600/3 |
| 2009/0264696 | A1 * | 10/2009 | White et al. ....................... 600/8 |
| 2009/0312593 | A1 * | 12/2009 | Drobnik et al. ................... 600/3 |

* cited by examiner

*Primary Examiner* — Navin Natnithithadha
*Assistant Examiner* — Sunita Reddy

(57) ABSTRACT

According to one general aspect, there is an double-balloon breast brachytherapy catheter comprising, an outer-balloon that is filled with a liquid substance or air via an out-balloon-filler; an inner-balloon that is filled with a liquid substance or air via an inner-balloon-filler, wherein the inner-balloon is inserted inside the outer-balloon; a plurality of radiation-tubes connected to an outside boarder of the inner balloon; a vacuum-tube that is wrapped around an exterior of the outer-balloon, wherein the vacuum tube is used to remove human fluids and air to create a void; and a flexible-shaft is connected to an upper-head, a proximal-tail and a distal-tip, wherein the upper-head is covered by the outer-balloon, the inner-balloon, the plurality of radiation-tubes and the vacuum-tube.

15 Claims, 8 Drawing Sheets

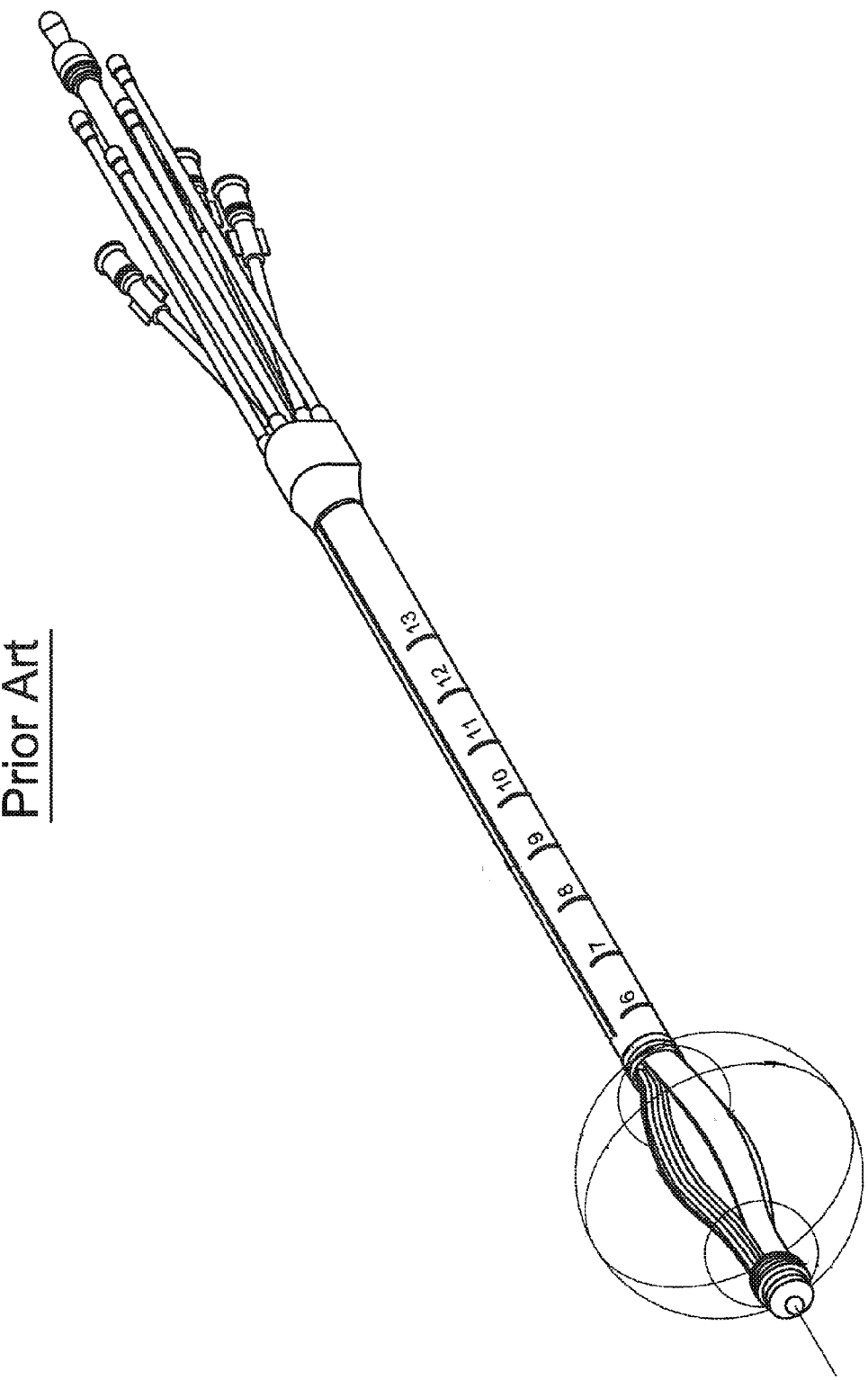

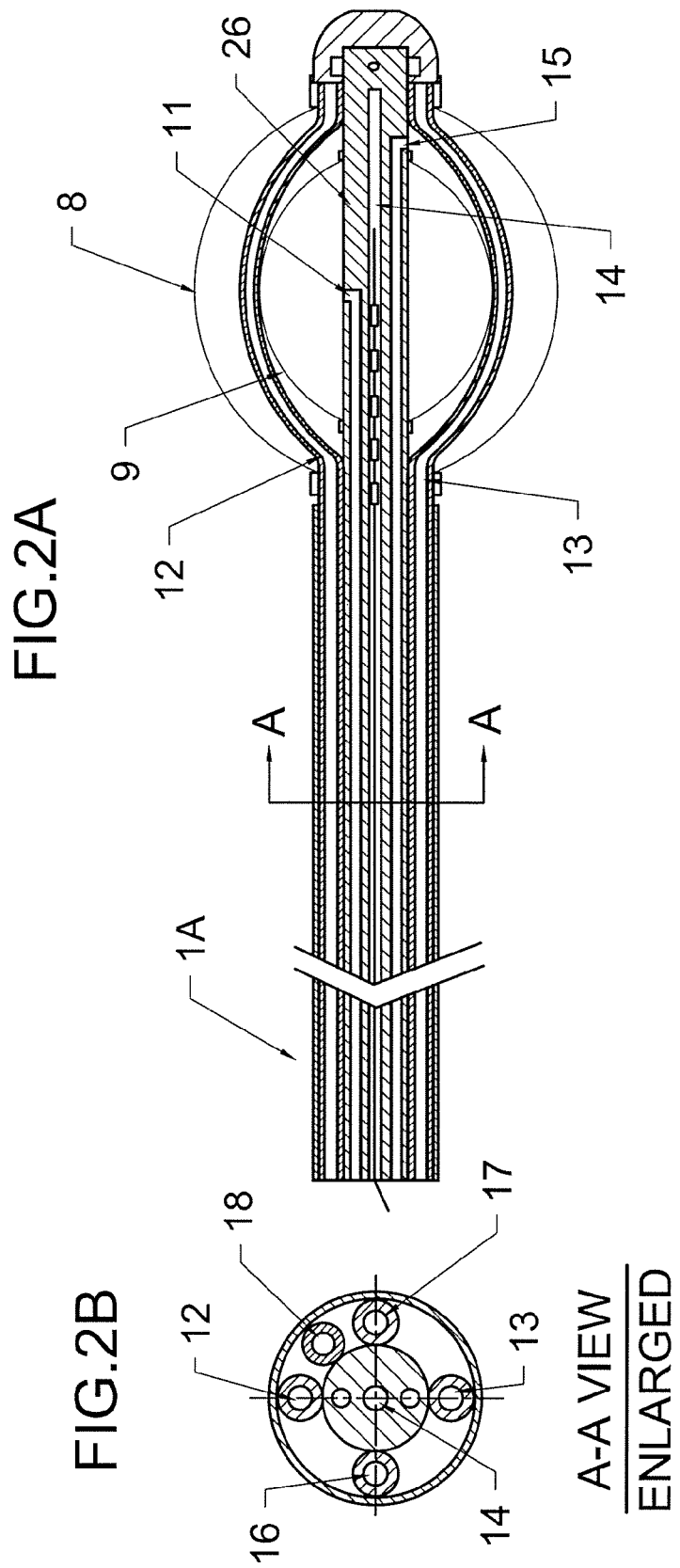

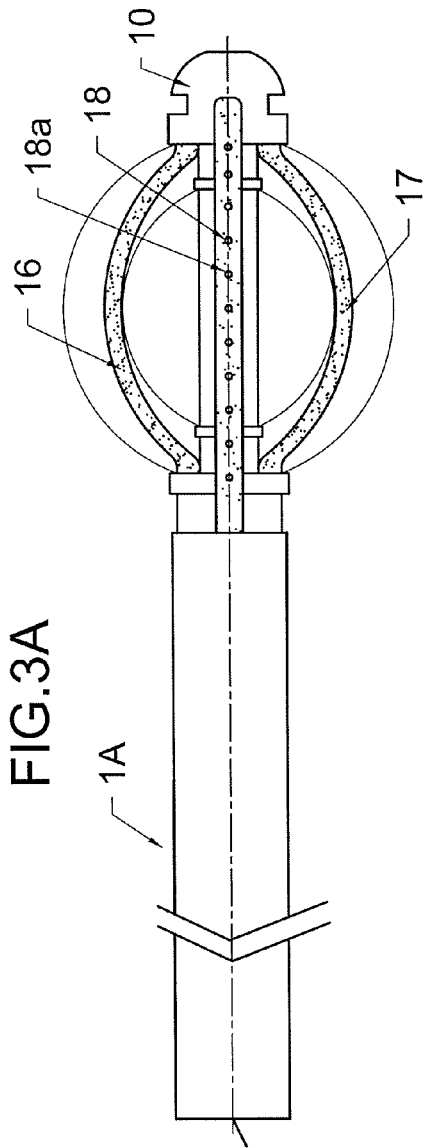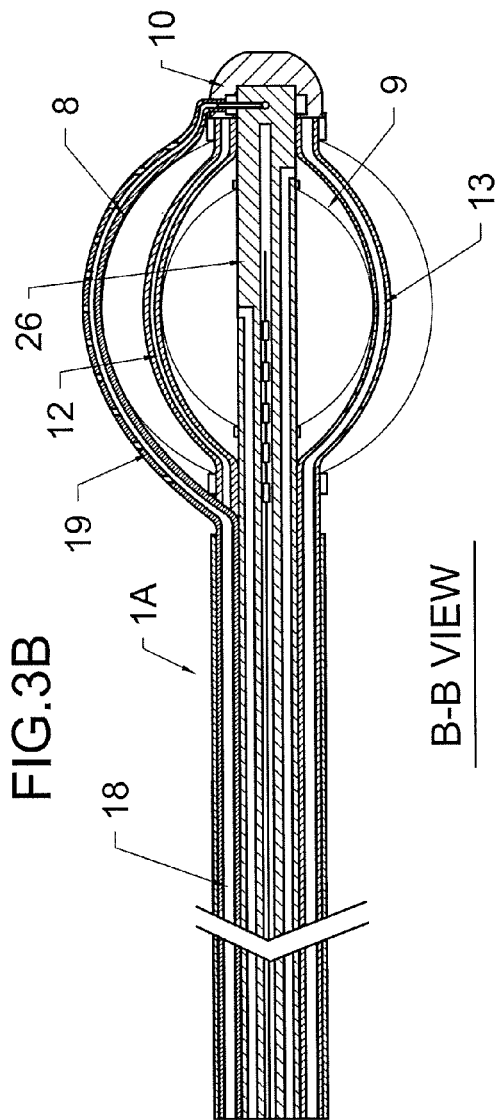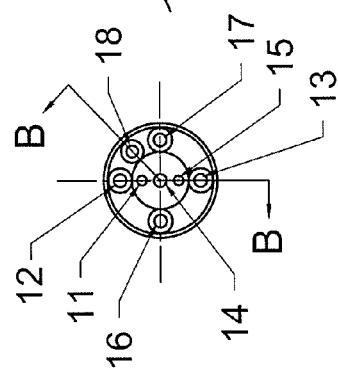

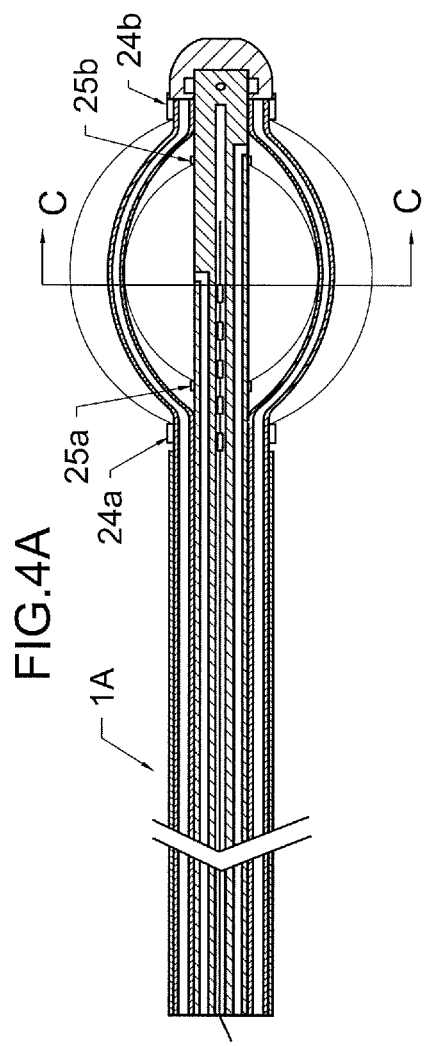
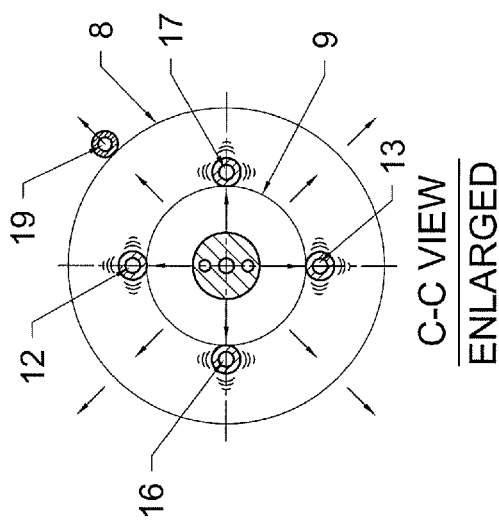

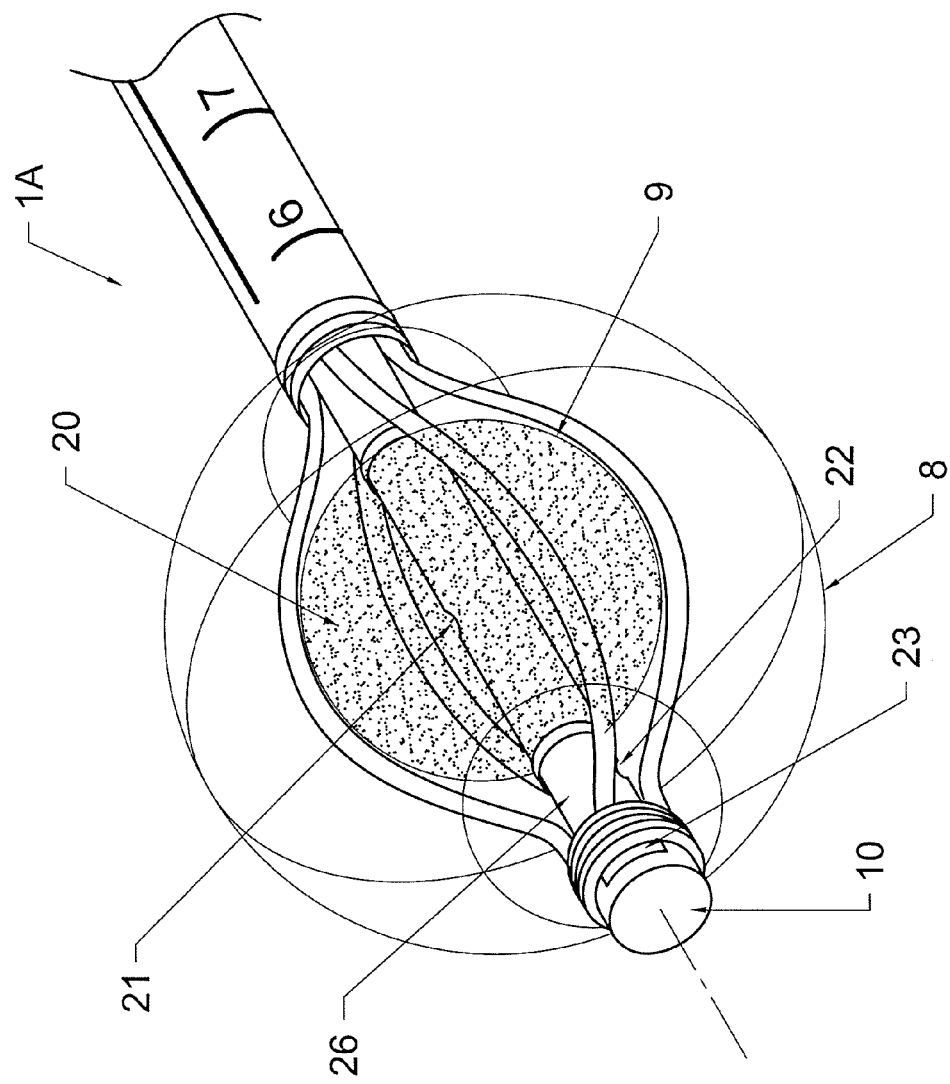

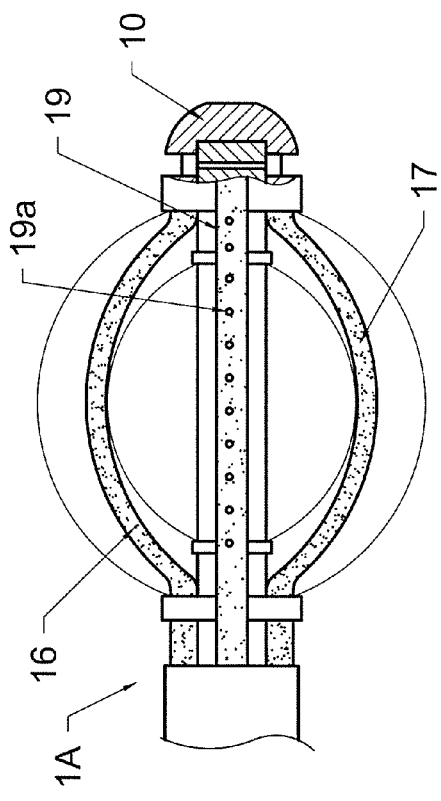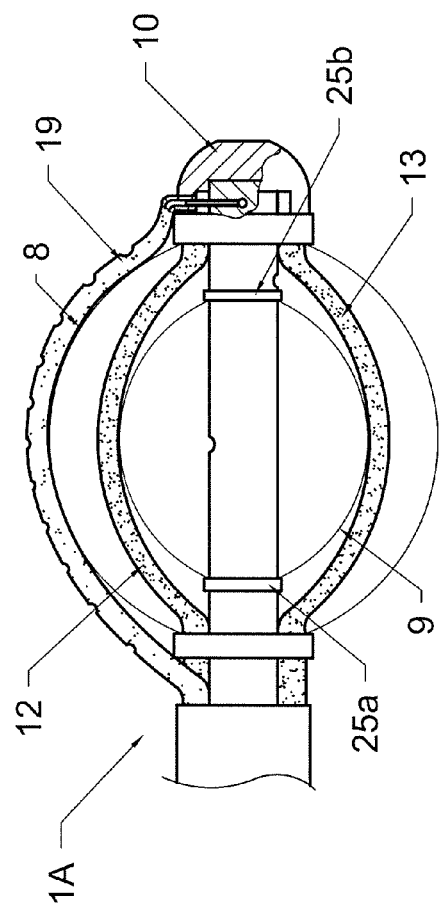

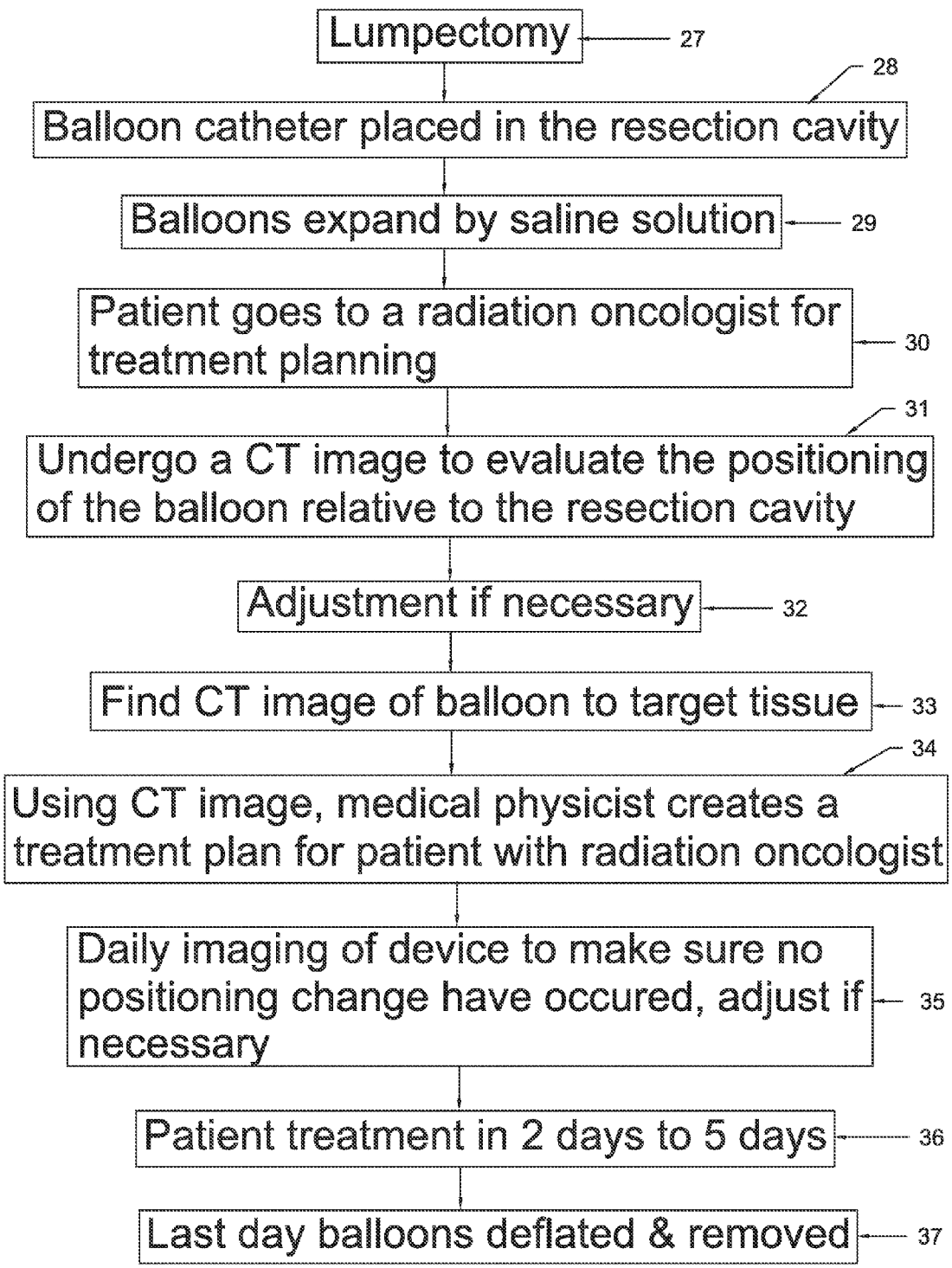

APPARATUS AND METHOD FOR PROVIDING A DOUBLE BALLOON BREAST BRACHYTHERAPY DEVICE

FIELD OF THE INVENTION

The invention generally relates to a device that allows for a conformal radiation dose distribution by allowing medical personnel to change the position and angle of a radiation source by inflating two balloons whereby an inner balloon positions treatment catheters within an outer balloon.

BACKGROUND

In diagnosing and treating malignant tumors, medical physicians all over the world have tried to create innovative devices designed to treat cancerous tumors in humans. At one time cancer could only be diagnosed when a tumor was big enough to see or feel. Now sophisticated imaging systems can identify tumors far earlier, often before any symptoms have even appeared thereby allowing for early treatment and potential cure. Over the years many different methods have been developed to treat cancer. For breast cancer, surgical approaches such as radical mastectomies were used to remove the breast, chest muscles and underarm lymph nodes—and were occasionally performed as early as the 19th century. The late 1940s brought the modified radical mastectomy, which spared the muscle tissue of the patient. In the 1970s, a more limited surgical option came into use, known as Breast Conservation Surgery, which focused on removal of the tumor and a small amount of surrounding tissue commonly referred to as a lumpectomy. In 1985, the lumpectomy combined with whole breast radiation therapy was found to be as effective as the mastectomy in terms of survival rates, but resulted in higher local relapse rates. As a result, medical research looked to provide other forms of combined surgical and localized radiation treatment options.

At the beginning of the 20th century, shortly after radiation began to be used for diagnosis and therapy, it was discovered that radiation could cause cancer as well as cure it. Many early radiologists used the skin of their arms to test the strength of radiation from their radiotherapy machines, looking for a dose that would produce a pink reaction (erythema) that looked like sunburn. They called this the "erythema dose," and this was considered an estimate of the proper daily fraction of radiation. In retrospect, it is no surprise that many developed leukemia.

Today, a lumpectomy is a common surgical procedure designed to remove a discrete lump, usually a benign or malignant tumor from an affected woman's breast or in rare occasions a man's breast. As the tissue removed is generally quite limited and the procedure relatively non-invasive, compared to a mastectomy, a lumpectomy is considered a viable means of "breast conservation" or "breast preservation" surgery with all the attendant physical and emotional advantages of such an approach.

In the past a few breast balloon brachytherapy devices have been developed. The most common types available are the Contura® a multi-lumen balloon breast brachytherapy device, and the MammoSite® breast brachytherapy device. Both devices are used in a procedure known as Accelerated Partial Breast Irradiation. Each device contains certain design drawbacks which will be described in the detail below.

An example of a brachytherapy applicator may be the "MammoSite® Radiation Therapy System" developed by Proxima Therapeutics, Inc., Alpharetta, Ga. 30005 USA. The MammoSite® RTS, a balloon catheter which is used in a high dose rate radiation procedure, was introduced specially for use in partial breast irradiation. The MammoSite catheter is inserted at the time of lumpectomy or within 30 days following surgery, remains in place during treatment and is deflated and removed at the end of treatment with mild pain medication. A solid radiation source is typically used; however, a liquid radiation source may also be used with a balloon device placed within a body cavity (e.g., Iotrex®, Proxima Therapeutics, Inc.) The solid radiation source may be removed following each treatment session, with the liquid source remaining in place as long as the balloon remains within the body cavity.

Clinical trials have shown efficacy of inflatable treatment delivery devices and systems such as MammoSite® RTS and similar devices and systems (e.g., GliaSite® RTS, Proxima Therapeutics, Inc.). However, radiation treatment delivered via these devices and systems can have deleterious effects on healthy tissue while providing the desired effects on cancerous tissue due to limited dose optimization inherent in the design. In a radiation treatment, care must be taken to direct the maximum therapeutic dose to diseased tissue while minimizing radiation dose to healthy tissue. For example, radiation treatment may be most effective when all surrounding tissue regions receive the same dose of radiation, and where the radiation dosage received by more distant tissue is as small and as uniform as possible. However because tissue cavities typically are not uniform or regular in their sizes or shapes and may be near critical structures such as skin, lung, or heart, radiation delivered via the aforementioned inflatable delivery devices can result in less than optimal dosages to different regions of surrounding tissue, creating "hot spots" and regions of relatively low dosage "cold spots".

In an effort to address this problem, another inventor has developed devices and systems to effectively draw adjacent tissue near a treatment device and thus enhance the treatment of the surrounding tissue (U.S. Pat. No. 6,923,754 B1 to Lubock, U.S. Pat. No. 6,955,641 B2 to Lubock). The Lubock patents described devices and systems that utilize vacuum to draw tissue surrounding a body cavity towards a treatment device placed within. The Lubock devices add a sheath or a fluid-permeable enclosure wall and a vacuum conduit to the Mammosite RTS or similar inflatable treatment delivery devices. These added elements create suction around the device, which draws tissue against the device surface within a body cavity, insuring a closer contact between the tissue and the device. Lubock devices claim that they can urge tissue into a desired orientation and position and form a uniform and controlled surface. This control over the distance, spacing, and the amount of tissue contact offers some advantages to the treatment of lining a body cavity.

However, despite small improvements, Lubock patents like the other prior arts, failed to provide physicians with better control over the optimization or shaping of the radiation dose within a body cavity. A common shortcoming of these applicators is that the source can only travel in or near a central catheter or centralized set of catheters within a cylindrical, or spherical balloon applicator. The existing balloon catheters only allow an offset from the center shaft of approximately 0 mm to 5 mm. Such designs limit the ability to maximize dose conformality and homogeneity which can only be maximized by allowing the treatment catheters to be placed significantly farther away from the central position. For example, after a surgery, doctors may find that the cavity wall is near sensitive regions which may have a higher sensitivity to radiation damage, including development of new cancerous tissue, than other areas surrounding the resection cavity. Doctors are always looking to deliver the maximum prescribed dose to the target region while minimizing dose to critical structures. Therefore, there is a need in the art to move the treatment catheters farther away from the central shaft of the balloon device to provide enhanced dose conformality, or dose shaping, allowing for greater flexibility in dose delivery to both target structures as well as those regions where reduced dose would be beneficial.

Design of intra-cavity applicators for brachytherapy is a challenging process, as the bio-mechanical and radiation dosimetry properties of the applicators must be such that they minimize the trauma to the patient during applicator insertion process; that they allow optimal radiation dose conformality to the tumor tissues; and that they provide adequate mechanical strength such that the location of the applicator is predictable throughout the course of treatment. Developments in medical imaging, such as CT, MRI, and PET imaging, have provided clinicians with means to identify tumors on patient images at earlier stages with increased confidence. The technical means to deliver this enhanced conformal dose however is currently severely limited by the available applicators. The present invention aims to overcome these limitations in order to achieve optimal radiation dose distribution to a variety of tumors in or near body cavities.

SUMMARY OF INVENTION

According to one general aspect, there is a double-balloon breast brachytherapy catheter comprising, an outer-balloon that is filled with a liquid substance or air via an outer-balloon-filler; an inner-balloon that is filled with a liquid substance or air via an inner-balloon-filler, wherein the inner-balloon is inserted inside the outer-balloon; a plurality of radiation-tubes connected to an outside b order of the inner balloon; a vacuum-tube that is wrapped around an exterior of the outer-balloon, wherein the vacuum tube is used to remove human fluids and air to create a void; and a flexible-shaft is connected to an upper-head, a proximal-tail and a distal-tip, wherein the upper-head is covered by the outer-balloon, the inner-balloon, the plurality of radiation-tubes and the vacuum-tube. The double-balloon breast brachytherapy catheter further comprising, the inner-balloon-filler increases volume of the inner-balloon that corresponds to a change in angle and length of the plurality of radiation-tubes, wherein the change in the angle and the length of the radiation-tubes reduces hot spots and cold spots. The double-balloon breast brachytherapy catheter further comprising, the vacuum-tube is attached to the distal-tip of the double-balloon breast brachytherapy catheter and allows for removal of the vacuum tube by releasing the vacuum-tube from the distal-tip. The double-balloon breast brachytherapy catheter further comprising: the outer-balloon is attached to the upper-head by an outer-ring and an inner-ring, wherein the outer-ring and the inner-ring are connected to opposite ends of the outer-balloon to provide a vacuum enclosure. The double-balloon breast brachytherapy catheter further comprising, the inner-balloon is attached to the upper-head by a mini-outer-ring and a mini-inner-ring, wherein the mini-outer-ring and the mini-inner-ring are connected to opposite ends of the inner-balloon to provide a vacuum enclosure within the outer-balloon. The double-balloon breast brachytherapy catheter further comprising, the proximal-tail contains a plurality of radiation-tubes-fillers, wherein the plurality of radiation-tubes-fillers are loaded with radioactive material used to treat unhealthy tissue.

In another aspect, there is a method of treating a patient by operating a double-balloon breast brachytherapy catheter comprising, filling a liquid substance or air via an outer-balloon-filler; filling a liquid substance or air via an inner-balloon-filler, wherein the inner-balloon is inserted inside an outer-balloon; altering a plurality of radiation-tubes angles and length by filling the inner-balloon-filler; removing human fluids and air to create a void around the double-balloon breast brachytherapy catheter; inserting a flexible-shaft in a human anatomy that is connected to an upper-head, a proximal-tail and a distal-end, wherein the upper-head is covered by the outer-balloon, the inner-balloon, the plurality of radiation-tubes and a vacuum-tube; and loading radioactive material into the radiation-tubes to provide dose treatment to a patient. The method of treating a patient wherein inserting the flexible-shaft in the human anatomy and then filling the outer-balloon to allow an approximate volume of the human anatomy to be treated. The method of treating a patient, wherein filling the outer-balloon and thereafter changing the angles and lengths of the radiation-tubes by filling an inner-balloon depending on a treatment plan for a patient.

DESCRIPTION OF THE DRAWINGS

FIG. 1 is an illustration of the prior art for the multi-lumen breast single balloon catheter.

FIG. 2A and FIG. 2B are illustrations of the internal structure of the shaft in the double-balloon breast catheter without the vacuum outer tube.

FIG. 3A, FIG. 3B and FIG. 3C are illustrations of the internal structure of the shaft in the double-balloon breast catheter with the vacuum outer tube.

FIG. 4A and FIG. 4B are illustrations of the internal structure of the double-balloon and the illustration of the flexible dose tubes.

FIG. 5 is an illustration of the internal balloon fill volume to demonstrate the flexible dose tubes.

FIG. 7A and FIG. 7B are illustrations of top and side views of the suction tube.

FIG. 8 is a flow-chart of the entire procedure for the lumpectomy and how to use the double-breast balloon.

DETAILED DESCRIPTION

Figure 6:
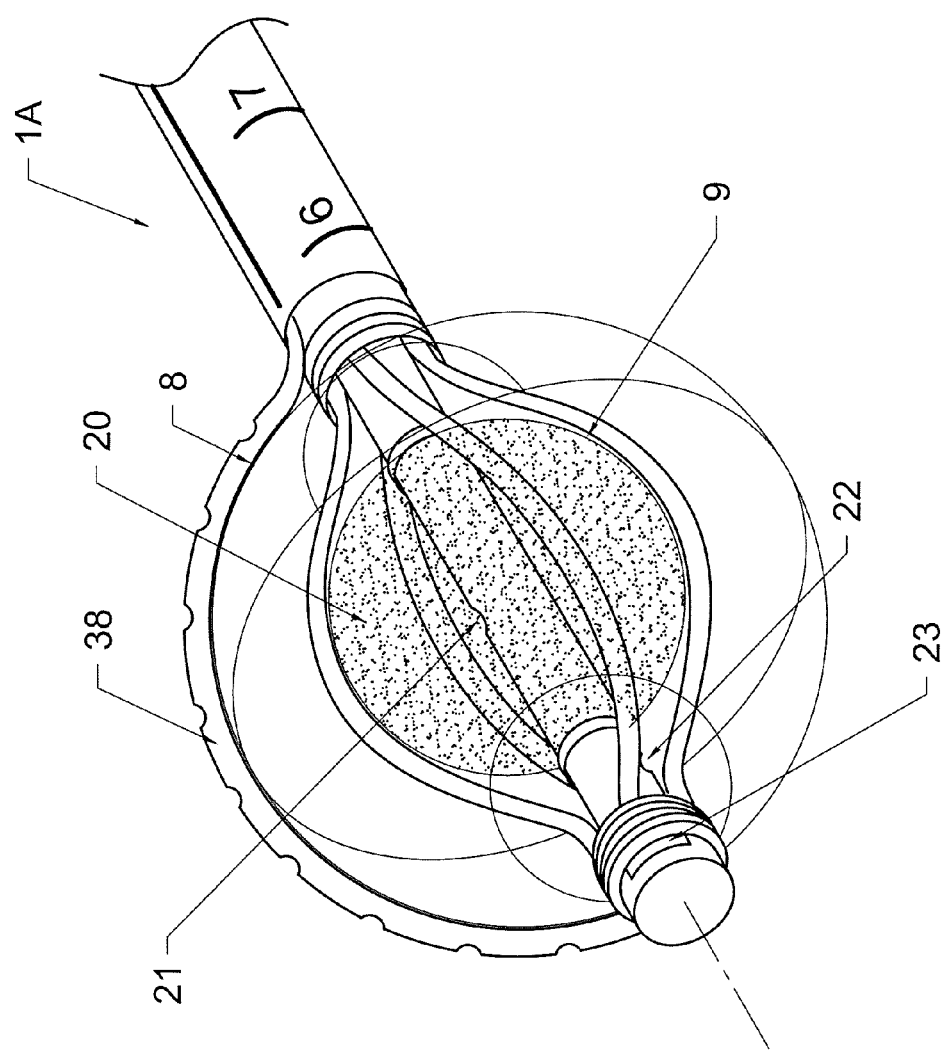
FIG. 6 is an illustration of the internal balloon fill volume with the outer vacuum tube with a collapsed outer balloon.

The invention generally relates to a device that allows for a conformal dose distribution by allowing medical personnel to change the location and angle of the radiation source by inflating two balloons in a catheter.

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

FIG. 2A shows ache double-balloon catheter 1A without the suction tube. The double-balloon allows medical personnel to provide an optimized dose distribution to a region of interest. The balloon structure may contain an outer-balloon 8 and an inner-balloon 9. The outer-balloon has a unique outer-balloon-fill port 15. Furthermore, the inner-balloon 9 may also have an inner-balloon-fill port 11. The two fill ports allow medical personnel to control the individual balloon sizes. This gives maximum amount of control for the medical personnel to distribute the optimal radiation dose to a patient. In embodiments of devices and methods having features, either of the balloon walls may comprise, but are not limited to, a polymer, such as a biocompatible polymer, preferably a radiation-resistant polymer. Suitable polymers include polyolefins such as polyethylene and polypropylene, polyurethanes, polyester, polyvinylchloride, polystyrene, thermoplastic polymers such as C-Flex® (consolidated Polymer Technologies, Inc., Clearwater Fla. 33762), block polymers such as Kraton™ (Kraton Polymers, Houston Tex. 77208), an ionomer such as Surlyn® (Dupont, Wilmington Del. 19880), nylon, latex rubber, and silicon rubber (e.g. SILASTIC™, Dow Corning, Midland, Mich.). Furthermore, the inner-balloon 9 is shown connected to four treatment catheters, however the design could use a greater or lesser number. For illustration purposes, FIG. 2A displays the top-radiation-tube 12 and the bottom-radiation-tube 13. The radiation-tubes 12, 13 will be positioned on the outside of the inner-balloon 9; however, for future modification, the radiation-tubes can also be inserted inside the inner-balloon. However, inserting the radiation-tubes into the inner balloon has great deficiency as described above. A device having features of the invention may further comprise multiple radiation-tubes. The multiple radiation-tubes can come in many different shapes, such as a whisk or may come in a form of a helix, where the radiation tubes are shaped in circle form around the shaft. The radiation-tubes may be configured to run longitudinally along a central shaft 26. During inflation of the balloon assemblies, the radiation-tubes may expand in the direction perpendicular to the shaft while spacing equally from each other and thus forming a three-dimensional catheter framework (or catheter assembly) for the balloon assemblies. The catheter framework may be uniform in size or regular in shape, such as a spherical, cylindrical or an elliptical shape, or may be nonuniform and irregular. A central catheter may also be inserted into the middle of the inner balloon assembly or the catheter framework. During the procedure, the radiation sources may be inserted into one or more of radiation-tubes following insertion into a body cavity. Radiation source may be solid or liquid and may be advanced within radiation-tubes by fluid or other mechanism, such as a wire, to preferred positions within a given radiation tube. The devices having features may be configured to deliver selective dosages of irradiation treatments to different tissue surrounding a body cavity based on the medical treatment needs of a patient. In addition, FIG. 2A has an A-A view illustrated in FIG. 2B. The A-A view of FIG. 2B illustrates a cross section of the double-balloon catheter bundle. Just for demonstrative purposes, the double-balloon catheter 1A of FIG. 2A has 4 radiation-tubes; however, is not limited to this number and many more radiation-tubes can be added. The A-A view of FIG. 2B illustrates a side-radiation-tube 16, a side-radiation-tube 17, the top-radiation-tube 12, the bottom-radiation-tube 13, a central radiation tube or measurement center 14, and a suction-tube 18. The central radiation tube 14 may also allow medical personnel to insert a MOSFET or linear array to measure the dose that is given to the patient.

FIG. 3A, FIG. 3B and FIG. 3C show the internal structure of the shaft in the double-balloon breast catheter 1A with a suction-tube 18. FIG. 3A shows the top view of the double-balloon catheter 1A with the suction-tube 18. The highlighted area shows the side-radiation-tube 16 and the side-radiation-tube 17 with the suction-tube 18. The suction-tube 18 is placed outside the outer-balloon 8 and connected to a distal end cap 10 that forms a distal-tip of the double-balloon catheter 1A. The distal end cap 10 allows for the release of the suction-tube 18 during the procedure or after the procedure. The suction-tube 18 is removed by medical personnel pulling out the suction-tube 18 separately from the double-balloon catheter 1A. FIG. 3B shows a side view taken along the section line B-B of FIG. 3C of the double-balloon catheter 1A with the suction-tube 18. The suction-tube 18 contains small holes 18a along the suction-tube 18. The suction-tube 18 allows for removal of fluid or air in the body while the procedure is being performed, and further provides that the surrounding skin is pulled tightly against the outer-balloon 8. For illustration purposes, the suction-tube 18 is on the outside of the outer-balloon 8. The top-radiation-tube 12, the bottom-radiation-tube 13, and the two side-radiation tubes 16, 17 are located on the outside of the inner-balloon 9. By utilizing the suction-tube 18 and inflating the inner-balloon 9 to position the radiation tubes 12, 13, 16 and 17 away from the central shaft 26, the dose distribution from the radiation source(s) can be optimized to provide the best possible treatment plan for the patient. The best distribution is possible by allowing the inner-balloon 9 to change the location and angle of the radiation tubes 12, 13, 16 and 17. The B-B cross-section view illustrated in FIG. 3B allows to demonstrate that the inner-balloon filler 11 and the outer-balloon-filler 15 are located in the center structure. Furthermore, the B-B view also contains the side-radiation-tube 16, the top-radiation-tube 12, the bottom-radiation-tube 13, the side-radiation-tube 17, an outer-vacuum-tube 19 and the suction-tube 18, as illustrated in FIG. 3B and FIG. 3C.

FIG. 4A and FIG. 4B show the internal structure of the double-balloon and a cross-section view of the expansion of the inner-balloon 9 that change in angle and location of the radiation tubes 12, 13, 16 and 17 when inflated and deflated. An inner-ring 24a and an outer-ring 24b are positioned at opposite ends of the outer-balloon 8 to provide a vacuum enclosure for the outer balloon 8. Also, an inner-balloon lock 25a or a mini-inner-ring and an outer-balloon lock 25b or a mini-outer-ring are positioned at opposite ends of the inner-balloon 9 to provide a vacuum enclosure or seal for the inner-balloon 9. The C-C view of FIG. 4B of the double-balloon catheter 1A shows the radiation tubes 12, 13, 16 and 17. Just for illustration purposes, there are four radiation-tubes, which are not limited to this number only; as the inner-balloon 9 is filled, the radiation-tubes 12, 13, 16 and 17 begin to move proportional to the increase in the size of the inner-balloon 9. The inner-balloon 9 expansion volume may vary depending on the fill volume of the outer-balloon 8. The change in the size and angle of the radiation tubes 12, 13, 16 and 17 allows for a more optimized dose distribution to the patient. The angle measurements of the radiation tubes 12, 13, 16 and 17 can be calculated depending on the amount of fluid inserted into the inner-balloon 9. This allows for medical personnel to optimize radiation dose homogeneity and conformality according to the patient's anatomy. In the radiation-tubes, a fluid radiation source may be any solution of radionuclide(s), e.g., a solution of I-125 or I-131. A radioactive fluid can also be produced using slurry of a suitable fluid containing small particles of a solid radionuclide, such as Au-198 or Y-90. Moreover, the radionuclide(s) can be embodied in a gel. One radioactive material useful is Iotrex™, a sterile single use, non-pyrogenic solution containing sodium 3-$C^{25}I$) iodo-4-hydroxybenzenesulfonate $C^{25}I$-HBS), available from Proxima Therapeutics, Inc. of Alpharetta, Ga.

FIG. 5 shows the internal balloon fill volume 20 to demonstrate the flexibility of the radiation tube, such as the radiation tubes 12, 13, 16 and 17. The inner balloon 9 is filled using the inside-filler 21. The inner-balloon 9 can be filled with either saline solution, air, or some type of radiation active liquid. The out-side-filler 22 is located outside of the inner balloon 9 on the central shaft 26, since the out-side-filler 22 fills the entire outer-balloon 8. The close up view of FIG. 5 of the double breast balloon of the double-balloon catheter 1A shows the internal components of the balloon.

FIG. 6 shows the internal balloon fill volume 20 with the outer-vacuum-tube 38 on the outer-balloon 8. The outer-vacuum-tube 38 is used to allow removal of fluids and air once the catheter is placed in the cavity. The vacuum-tube 38 may conform to the shape of the outer-balloon 8. For additional functionality, the vacuum-tube 38 may be removed by the medical personnel by pulling on the tube, thus, allowing removal during or following the placement procedure. The vacuum-tube 38 can be attached to the outer-balloon 8 if a design preference is requested by medical personnel; however, vacuum-tube 38 is not limited to being attached. Another design of the double-balloon catheter 1A can be the vacuum-tube 38 not being attached to the outer-balloon 8.

FIG. 7A and FIG. 7B show the top and side views of the vacuum-tube 19. FIG. 7A shows the top view of the outer-vacuum-tube 19. The vacuum-tube 19 has holes 19a along the vacuum-tube 19 to remove fluids or air that may be in the cavity. The vacuum-tube 19 permits the outer-balloon 8 to be as close to the human skin or tissue as possible. The vacuum-tube 19 is then connected to the end cap 10 of the double-balloon catheter 1A. FIG. 7B shows the side view of the double-balloon catheter 1A with the vacuum-tube 19. The inner-balloon-locks 25a and 25b create a seal for the inner-balloon 9. The inner-balloon 9 can be inflated without inflation of the outer balloon 8 if need be in very small cavities or where the increase in volume by the outer-balloon 8 may damage or rupture some of the internal tissue. The vacuum-tube 19 is connected to the end cap 10 of the double-balloon catheter 1A. The vacuum-tube 19 may be released from the end cap 10 by a mechanical lever or button 23 (FIGS. 5, 6), initiated by the medical personnel.

FIG. 8 shows a general procedure for ache lumpectomy and how to use the double-balloon device, such as the double-balloon catheter 1A. Lumpectomy 27 is the removal of the breast tumor and some of the normal surrounding tissue. Lumpectomy is a form of "breast-conserving" or "breast preservation" surgery. There are several names used for breast-conserving surgery: biopsy, lumpectomy, partial mastectomy, re-excision, quadrantectomy, or wedge resection. Technically, a lumpectomy is a partial mastectomy, because part of the breast tissue is removed. The catheter, such as the double-balloon catheter 1A, is initially provided deflated to allow minimal diameter to allow for insertion through a small incision in the breast. After a few days or weeks following the removal of the tumor, the double-balloon breast catheter is placed in the resection of cavity 28 and expanded 29. To evaluate the satisfactory deployment and positioning of the device the patient will undergo an imaging procedure such as an MRI or CT, usually performed by the radiation oncologist. Depending on the tumor area, the medical personnel can inflate the outer-balloon 8 or the inner-balloon 9. If the area removed is large, the medical personnel may want to inflate the outer-balloon 8 first; thus, allowing for internal structural support. On the other hand, if the area is small, the medical personnel may want to inflate the inner-balloon 9 first to allow the radiation-tubes to be a certain size and thereafter inflate the outer-balloon 8. The outer-balloon 8 may have grooves along the outer wall. This will allow tissue to seep into the grooves on the outer-balloon wall and not allow the balloon to rotate inside the patient. Once the balloon is fixed, the patient goes to a radiation oncologist for treatment planning 30. The plan will be determined by the radiation oncologist. During this time, the patient will be undergoing a CT or MRI image to evaluate the positioning of the balloon relative to the resection cavity 31. The images will allow the medical personnel to make changes or modify the position of the catheter 32. When the catheter is in optimal position inside the human cavity 33, such as by finding a CT image of the balloon to target tissue, a medical physicist can create a treatment plan for the patient with radiation oncologist 34 prescribing the dose. The radiation treatment can vary depending on cavity location relative to other sensitive critical structures. The double-balloon breast catheter will remain in the patient for the entire course of treatment. During the course of treatment the patient may receive daily imaging of the device 35 to make sure no device positioning changes have occurred relative to the original image which was used to plan the case. If changes have occurred adjustments can be made if necessary 35. On average, a patient will receive a fractionated treatment typically 2 fractions per day over three to five days of treatment 36, and one to four hours a day. During the last day, the balloon will be removed of all fluids and extracted from the human cavity 37.

A number of exemplary embodiments have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A double-balloon breast brachytherapy catheter, comprising:
    an outer-balloon configured to be filled with a liquid substance or air via an outer-balloon-filler to selectively adjust an outer balloon size;
    an inner-balloon configured to be filled with a liquid substance or air via an inner-balloon-filler to selectively adjust an inner balloon size, wherein said inner-balloon is positioned inside said outer-balloon; and
    a plurality of flexible radiation-tubes positioned by said inner-balloon and each of said flexible radiation-tubes configured to change in angles and lengths proportional to a size of said inner-balloon by filling said inner-balloon via said inner-balloon-filler with the liquid substance or air, a change in size of said inner-balloon changing the angles and the lengths of said flexible radiation-tubes as said flexible radiation-tubes are moved into a radiation-delivery position by said inner-balloon,
    wherein the outer balloon size and the inner balloon size are selectively adjusted independent of each other, and the radiation-delivery position is varied by said inner-balloon, to optimize radiation delivery.

2. The double-balloon breast brachytherapy catheter according to claim 1, wherein
    said inner-balloon-filler increases a volume of said inner-balloon to increase the size of said inner-balloon to a corresponding said inner balloon size that provides a corresponding change in an angle and a length of each of said flexible radiation-tubes.

3. The double-balloon breast brachytherapy catheter according to claim 1, further comprising:
    a vacuum-tube attached to a distal-tip of said double-balloon breast brachytherapy catheter to allow for removal of fluids or air from around the distal-tip.

4. A method for treating a patient by operating a double-balloon brachytherapy catheter, comprising the steps of:

filling a liquid substance or air into an outer-balloon via an outer-balloon-filler to selectively adjust and achieve an outer balloon size;

filling a liquid substance or air into an inner-balloon via an inner-balloon-filler to selectively adjust and achieve an inner balloon size, wherein said inner-balloon is positioned inside said outer-balloon, a plurality of flexible radiation-tubes being positioned within said outer-balloon and positioned by said inner-balloon;

changing angles and lengths of each of said flexible radiation-tubes proportional to a size of said inner-balloon by filling said inner-balloon via said inner-balloon-filler with the liquid substance or air, a change in size of said inner-balloon changing the angles and the lengths of said flexible radiation-tubes;

selectively controlling the outer balloon size and the inner balloon size mutually independently; and loading radioactive material into at least one of said plurality of flexible radiation-tubes to provide a radiation dose treatment.

5. The method of claim 4, further comprising the step of:
selectively filling said outer-balloon to fill a cavity volume for the radiation dose treatment.

6. The method of claim 5, further comprising the step of:
positioning said flexible radiation tubes by changing the angles and the lengths of each of said flexible radiation-tubes by filling said inner-balloon with the liquid substance or air to provide a corresponding said inner balloon size that corresponds to a radiation-delivery position to optimize radiation delivery based on a treatment plan.

7. The method of claim 6, further comprising the step of:
removing by a vacuum-tube fluids or air from a cavity receiving the double-balloon brachytherapy catheter.

8. The method of claim 4, further comprising the step of:
removing by a vacuum-tube fluids or air from a cavity receiving the double-balloon brachytherapy catheter.

9. The method of claim 4, further comprising the steps of:
inserting into a cavity a shaft that is connected to said outer-balloon, said inner-balloon, said flexible radiation-tubes and a vacuum-tube; and
removing fluids or air from the cavity receiving the double-balloon brachytherapy catheter using the vacuum-tube.

10. A double-balloon brachytherapy catheter, comprising:
an outer-balloon configured to be filled with a liquid substance or air to selectively adjust an outer balloon size;
an inner-balloon configured to be filled with a liquid substance or air to selectively adjust an inner balloon size, wherein said inner-balloon is positioned inside said outer-balloon; and
a plurality of flexible radiation-tubes positioned by said inner-balloon and adapted to receive a corresponding radiation source, each of said flexible radiation-tubes configured to change in angles and lengths proportional to a size of said inner-balloon by filling said inner-balloon with the liquid substance or air, a change in size of said inner-balloon changing the angles and the lengths of said flexible radiation-tubes as said flexible radiation tubes are moved into a radiation-delivery position by said inner-balloon, the plurality of said flexible radiation-tubes being positioned within said outer-balloon and adapted to move into the radiation-delivery position within said outer-balloon by the filling of said inner-balloon with the liquid substance or air,
wherein said inner-balloon selectively positions said flexible radiation-tubes within said outer-balloon, the radiation-delivery position is selectively varied by said inner-balloon, and the outer balloon size and the inner balloon size are selectively adjusted independent of each other, to optimize radiation delivery by the corresponding radiation source.

11. The double-balloon brachytherapy catheter according to claim 10,
wherein a volume of said inner-balloon is selectively adjusted to a corresponding said inner balloon size that provides a corresponding change in an angle and a length of each of said flexible radiation-tubes to correspond to the radiation-delivery position.

12. The double-balloon brachytherapy catheter according to claim 10, wherein
a volume of said inner-balloon is selectively adjusted to a corresponding said inner balloon size that provides a corresponding change in a location and an angle of each of said flexible radiation-tubes to correspond to the radiation-delivery position.

13. The double-balloon brachytherapy catheter of claim 10, further comprising:
a vacuum-tube attached to a distal-tip of said double-balloon brachytherapy catheter to allow for removal of fluid or air from around the distal-tip.

14. The double-balloon brachytherapy catheter of claim 10, further comprising:
a vacuum-tube positioned outside of said outer-balloon to remove fluid or air from around the outside of said outer-balloon.

15. The double-balloon brachytherapy catheter of claim 10, further comprising:
a vacuum-tube to remove fluids or air from a cavity receiving the double-balloon brachytherapy catheter.

* * * * *